United States Patent [19]
Berg

[11] Patent Number: 5,820,612
[45] Date of Patent: Oct. 13, 1998

[54] CATHETER JOINT WITH COUNTERBORE

[75] Inventor: Todd A. Berg, Hugo, Minn.

[73] Assignee: SciMed Life Systems, Inc., Maple Grove, Minn.

[21] Appl. No.: 392,609

[22] Filed: Feb. 22, 1995

Related U.S. Application Data

[63] Continuation of Ser. No. 178,661, Jan. 7, 1994, abandoned.

[51] Int. Cl.⁶ .................................................. A61M 25/00
[52] U.S. Cl. ........................................... 604/282; 403/185
[58] Field of Search ..................... 604/264, 280, 604/282, 283, 905; 128/565–658; 403/185, 268, 294, 332

[56] References Cited

U.S. PATENT DOCUMENTS

| | | | |
|---|---|---|---|
| 3,485,234 | 12/1969 | Stevens ........................................ | 128/2 |
| 4,210,478 | 7/1980 | Shoney ..................................... | 156/242 |
| 4,419,095 | 12/1983 | Nebergall et al. ......................... | 604/96 |
| 4,516,970 | 5/1985 | Kaufman et al. ......................... | 604/270 |
| 4,531,943 | 7/1985 | Van Tassel et al. ..................... | 604/280 |
| 4,588,399 | 5/1986 | Nebergall et al. ....................... | 604/280 |
| 4,842,590 | 6/1989 | Tanabe et al. ........................... | 604/282 |
| 4,863,442 | 9/1989 | DeMello et al. .......................... | 604/282 |
| 4,898,591 | 2/1990 | Jang et al. ............................... | 604/282 |
| 4,920,980 | 5/1990 | Jackowski ............................... | 128/786 |
| 5,017,259 | 5/1991 | Kohsai .................................... | 156/294 |
| 5,078,702 | 1/1992 | Pomeranz ................................ | 604/280 |
| 5,160,559 | 11/1992 | Scovil et al. ........................... | 156/73.6 |
| 5,234,416 | 8/1993 | Macaulay et al. ....................... | 604/282 |

*Primary Examiner*—Corrine M. McDermott
*Attorney, Agent, or Firm*—Crompton, Seager & Tufte, LLC

[57] ABSTRACT

An improved joint for connection of two segments of intravascular catheters of the type having an inner tubular member defining a lumen, an outer tubular member surrounding said inner member, and a support member mounted between the tubular members to provide rigidity to the flexible catheter. The improved joint is also used for connecting a similar type catheter to a desired tip. The preferred embodiment comprises a counterbore in the end of the catheter from which approximately all of the inner tubular member and support member have been removed. The counterbore is adapted to mate with a male portion on either the second catheter or the tip to form an overlap type joint.

10 Claims, 3 Drawing Sheets

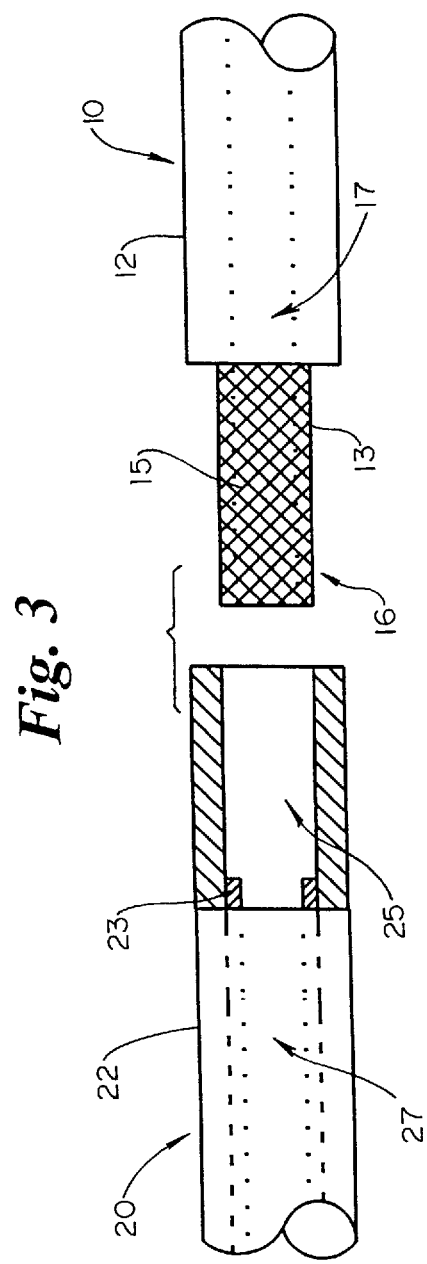

CATHETER JOINT WITH COUNTERBORE

CROSS REFERENCES TO CO-PENDING APPLICATIONS

This application is a continuation of U.S. Ser. No. 08/178,661, filed Jan. 7, 1994, entitled "IMPROVED CATHETER JOINT WITH COUNTERBORE", now abandoned.

BACKGROUND OF THE INVENTION

1. Field of the Invention

The present invention generally relates to the field of intravascular medicine and more particularly to the field of catheters such as guide catheters used for the placement of medicines and medical devices within the body.

2. Description of the Prior Art

The use of intravascular catheters for treatment of the body is well known in the field of medicine. The need for a choice of catheter sizes and types has grown rapidly as the techniques for their use have been greatly improved and the types of medical uses have expanded in keeping with the technological advances.

Prior art catheters often comprise a pair of congruent tubes, the inner one defining a lumen. A hub is connected at the proximal end of the tubes which in addition to providing access to the lumen for fluids and the like, is often used to provide torques and other necessary pressures to the tubes during their placement within the body. A tip of a selected design is placed at the distal end of the tubes. Flexibility is an essential part of the catheter so that it may be successfully torqued, pushed and pulled on its way through the vascular passage to the desired site in the body. For control of the catheter and to prevent its kinking from excessive flexing a certain amount of rigidity is required. The prior art catheters often meet this need for rigidity by adding a support member between the two tubes. This support member may comprise a braid of metal wire wrapped around the inner tube, and often imbedded within the outer tube.

As specific examples of the type of prior art catheters described above, note U. S. Pat. No. 3,485,234, issued Dec. 23, 1969, to R. C. Stevens, for TUBULAR PRODUCTS AND METHOD OF MAKING SAME; and, European Patent Application, Publication No. 0 277 366/A1, Priority Jun. 1, 1987, by Bruce H. Ward, for GUIDING CATHETER AND METHOD FOR MAKING IT. Each of these references teaches, in general, the prior art type of catheter discussed above.

One problem area in the field of this invention is that of the joinder of catheters to segments of other catheters or to a selected distal tip. The most commonly used form of joinder is that of the butt joint, which form of joint commonly uses plastic fusion as its adhesive. A disadvantage of the butt type of joint is that due to its small bonding surface area it has limited strength, it being well known that the bond strength is directly related to the surface contact area of the joint.

One attempt to overcome the disadvantage described above comprises the use of a lap joint type joint. Such a joinder is described in U.S. Pat. No. 4,863,442, issued Sep. 5, 1989 to R. M. DeMello et al, for SOFT TIP CATHETER, which teaches using a lap joint for tip connection to a catheter. The DeMello reference teaching includes a step in the distal end of a catheter forming a male portion of a lap joint, the portion including the support member or braid. The tip provides the female portion of the joint. While this prior art improves on the butt joint type of connection by providing a greater cross-sectional area at the joinder, it does not address the problems attendant in using the overlap type of connection with the presence of metal braid, Teflon linings and other polymers, for example, all of which may be non-heat bondable, thus causing difficulties in heat bonding the overlap joint.

SUMMARY OF THE INVENTION

The apparatus and method of this invention overcomes this latter mentioned difficulty by providing a counterbore at one end of a catheter to remove the support braid and other materials and form one portion of mating members of a lap joint. In the case of joinder to a desired tip, the tip is provided with a stepped down portion having a diameter sized to fit within the counterbore and thus serving as a second mating member of the lap joint; and in the case of joinder to a segment of another catheter, a step is ground into the end of the segment to similarly form a stepped down portion of a desired diameter.

This use of the counterbore in a lap joint provides improved strength and integrity, and in the case of joinder to a tip also provides for a flexibility transition area, a feature found to have a clinical advantage.

BRIEF DESCRIPTION OF THE DRAWINGS

Other objects of the present invention and many of the attendant advantages of the present invention will be readily appreciated as they become better understood by reference to the following detailed description when considered in connection with the accompanying drawings, in which like reference numerals designate like parts throughout all figures:

FIG. 3 is a partial cross-sectional plan view of segments of two catheters prepared for joinder utilizing the overlap joint apparatus of this invention;

DETAILED DESCRIPTION OF THE PREFERRED EMBODIMENT

Figure 1:
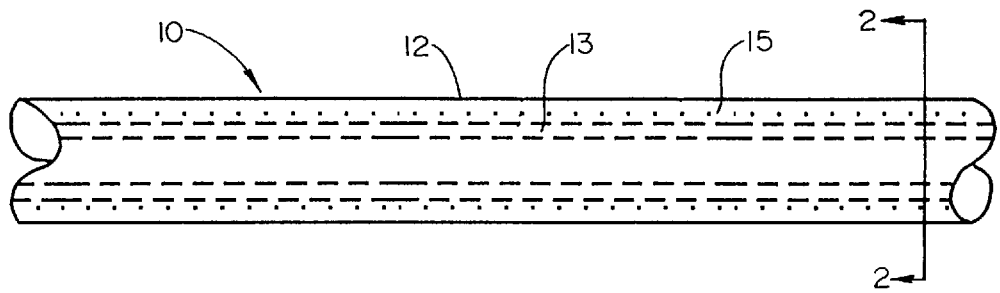
FIG. 1 is a plan view showing a portion of a catheter.

FIG. 1 shows a thin-walled guide catheter 10. Catheter 10 comprises an outer tubular member 12 which surrounds and is coaxial with an inner tubular member 13 shown in dashed phantom lines. A support member 15 is shown in dotted phantom lines. Member 15 is a preferably a metal braid which also surrounds and is coaxial with member 13.

Figure 2:
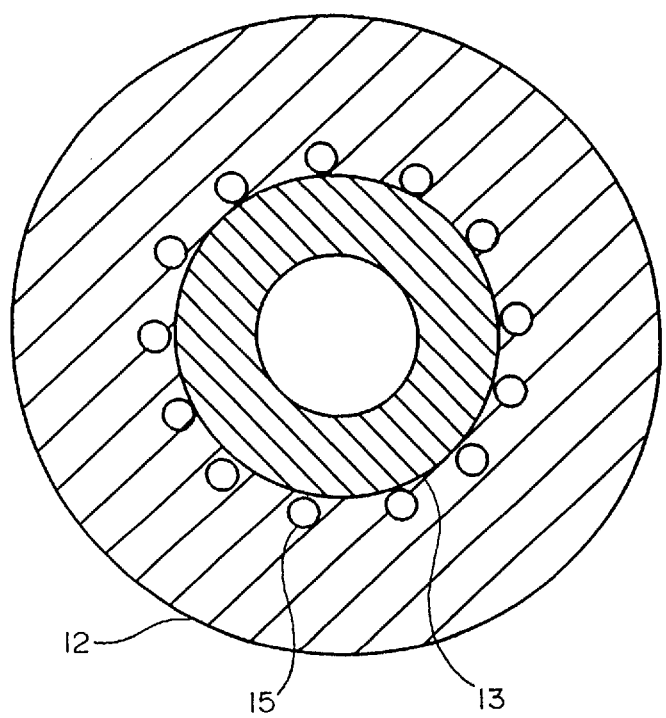
FIG. 2 is another plan view of a portion of the catheter of FIG. 1 showing an end section taken along the line 2—2.

FIG. 2 is an end view of the catheter of FIG. 1 taken along the line 2—2. This shows the preferred congruency of members 12 and 13, and the positioning of braid 15 within the catheter.

In general, the catheter shown in FIGS. 1 and 2 is well known in the prior art and to practitioners in the field of intravascular catheterization.

FIG. 3 shows a pair of catheter segments 12 and 22 which have been prepared for joining their respective catheters 10 and 20, using the joinder apparatus of this invention. Catheters 10 and 20 will most commonly have differing flexibility ratings. Segment 12 is shown having one end with outer tubular member 12 abraded or ground down to a stepped portion 16 of reduced diameter that includes support member 15 and core or tubular member 13. As used herein, the terms "abraded" and "ground" have the same meaning. Segment 12 defines a central lumen 17 as shown. Though portion 16 is shown in this drawing as being ground down to expose braid 15, it should be recognized that within the scope of this invention stepped portion 16 could be of a diameter such that braid 15 is still covered by outer member 12. It will be apparent that the phantom lines for member 13 and support member 15 have been omitted for purposes of clarity.

Segment 22 of catheter 20 is shown in partial cross-section. The cross-section reveals that a counterbore 25 has been drilled into segment 22. Counterbore 25 has a diameter sufficient to assure that any support member such as a braid (not shown), as well as any core such as inner tubular member 23, have been completely removed from bore 25. Member 23 defines a central lumen 27 which is preferably sized to match lumen 17. The diameter of counterbore 25 is also sized to receive stepped portion 16 of catheter 10, which portion 16 preferably abuts against the wall formed by the remainder of member 23 at the end of the bore.

The joint of this invention is finalized when the prepared ends of catheters 10 and 20 are mated such that portion 16 lies within bore 25 (preferably abutting member 23), at which time a heat bonding process is applied for completion of the joint. Preferably, the lengths of portion 16 and bore 25 are approximately equal. It has been found that portion 16 could have a length slightly less than that of bore 25 without significantly effecting the integrity of the resulting joint. It has also been found that for the preferred embodiment of this invention the length of bore 25 should be approximately 0.100 inches, and within the range of from 0.020 to 0.250 inches.

Figure 4A:
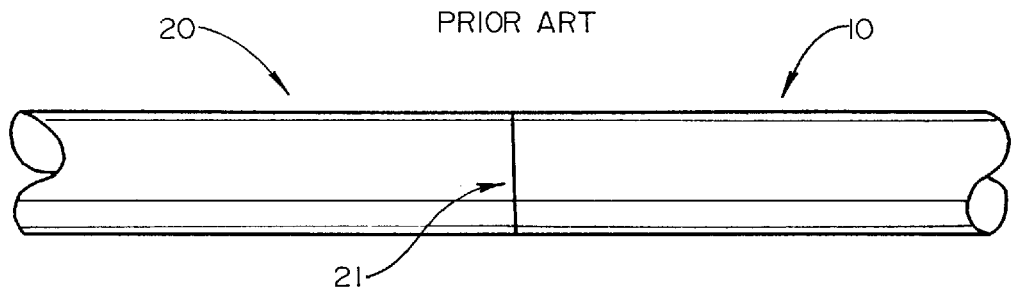
FIGS. 4a and 4b are plan views each showing a pair of joined catheter segments for visually comparing the prior art joint of FIG. 4a with the joint of this invention shown in FIG. 4b.
Figure 4B:
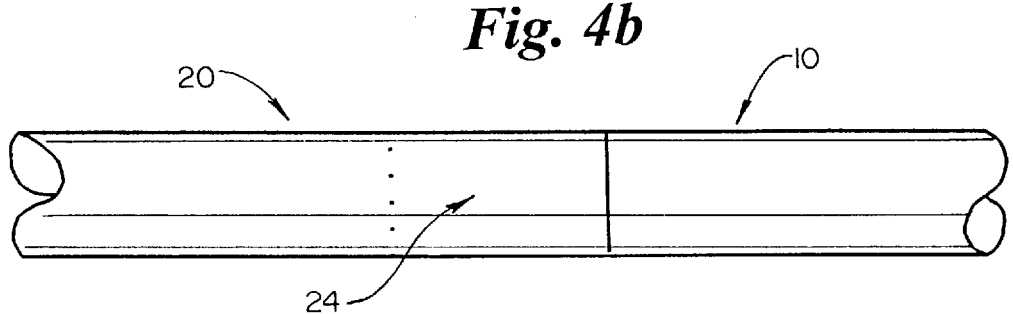

Referring now to FIGS. 4a and 4b there are shown the completed prior art butt joint connection 21 of FIG. 4a and the completed overlap joint 24 of this invention in FIG. 4b. The length of lap joint 24 is shown with the use of a phantom line. Though both of joints 21 and 24 are shown achieving connection of catheters 10 and 20 without causing bumps or other undesirable deformations along the outer or inner surface of the resulting catheter, a comparison of FIGS. 4a and 4b clearly reveals that joint 24 of this invention results in a much greater cross-sectional area of joinder than does the prior art joint 21. Thus joint 24 of this invention provides for significantly increased strength an overall integrity of joinder.

Figure 5:
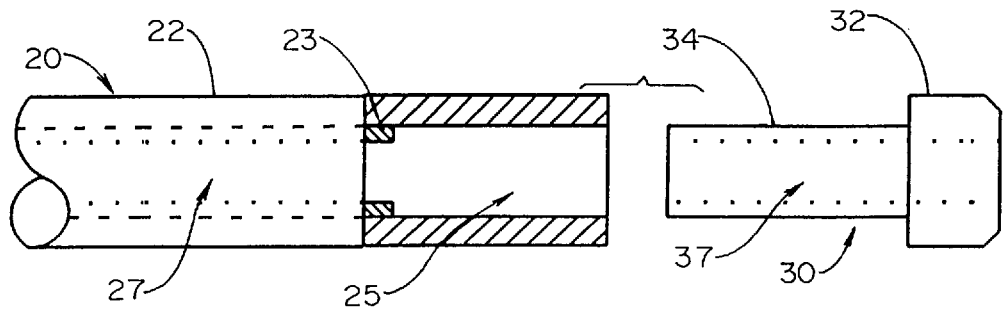
FIG. 5 is a partial cross-sectional plan view of a catheter segment and a catheter tip prepared for joinder utilizing the overlap joint apparatus of this invention.

Referring now to FIG. 5 there can be seen another preferred embodiment of this invention in which catheter 20 is to be joined to a tip 30. Catheter 20 is again shown in partial cross-section. As in FIG. 3, one end of catheter 20 has been counter bored to create a counterbore 25 from which all braid or other support member has been removed, as well as all of the inner core or tubular member 23. Member 23 defines a central lumen 27 as shown partly in phantom lines.

Tip 30 has a head portion 32 and a male joinder portion 34 of lesser diameter than head 32. Portion 34 may be formed by an abrasion or grinding or other removal process, as was portion 16 of FIG. 3. The diameter of portion 34 is sized to fit into bore 25 and the length of portion 34 is preferably approximately equal to that of bore 25. Portions 32 and 34 define a central lumen 37 preferably sized to match lumen 27.

As in the description of the joint in FIGS. 3 and 4b above, when portion 34 has been placed into counterbore 25 and the joint has been bonded, the result will be an overlap joinder of much greater cross-sectional area than that of the prior art butt type joinder. Thus the lap joint connection of catheter 20 to tip 30 results in a connection with significantly greater strength and integrity. Another advantage of the apparatus of this invention as depicted in FIG. 5 is that the complete absence of any braid or other support member from the area of the joint provides for a region of flexibility transfer, which feature has been found to provide a clinical advantage.

Having thus described the preferred embodiments of the present invention, those of skill in the art will readily appreciate the other useful embodiments within the scope of the claims hereto attached.

I claim:

1. In a catheter apparatus having at least outer and inner congruent generally tubular structures and a support member mounted between said tubular structures, wherein said catheter apparatus includes another selected device joined thereto, the improvement comprising: an improved joint for joining the catheter apparatus to said selected device wherein said selected device has a male member, said joint including, a. a counterbore at one end of the catheter apparatus;
   b. the counterbore having sufficient diameter to effectively remove all of the support member and the inner tubular structure from within the counterbore; and
   c. the counterbore adapted to form an overlap connection with the male member when received therein on the selected device.

2. The apparatus of claim 1 in which the selected device is another catheter apparatus.

3. The apparatus of claim 2 in which the male member comprises a step in the second catheter apparatus for reducing the diameter of the second catheter apparatus for a predetermined stepped region between the step and one end of the second catheter apparatus, the stepped region adapted to mate with and be selectively joined to the counterbore of the first catheter apparatus.

4. The apparatus of claim 3 in which the stepped region has a length approximately equal to the length of the counterbore.

5. The apparatus of claim 1 in which the selected device is a catheter tip.

6. The apparatus of claim 3 in which the male member comprises a step in the catheter tip for reducing the diameter of the catheter tip for a predetermined stepped region between the step and one end of the catheter tip, the stepped region adapted to mate with and be selectively joined to the counterbore of the first catheter apparatus.

7. The apparatus of claim 6 in which the stepped region has a length approximately equal to the length of the counterbore.

8. The apparatus of claim 1, 2 or 5 in which the male member has length approximately equal to the length of the counterbore.

9. The apparatus of claim 4 or 7 in which the length of the counterbore is approximately 0.125 inches.

10. A catheter assembly comprising:

a. a proximal member having a proximal end and a distal end comprising at least one outer and one inner congruent generally tubular structures and a support member mounted therebetween;
   b. a distal member having a proximal end and a distal end with a mating male member located at the proximal end of the distal member; and c. a counterbore extending proximally from the distal end of the proximal member; the counterbore having sufficient diameter to effectively remove all of the support member and the inner tubular structure from the proximal member within the counterbore; said mating male member received within said counterbore so that the counterbore forms an overlap connection with the mating male member of the distal member.

* * * * *

UNITED STATES PATENT AND TRADEMARK OFFICE
CERTIFICATE OF CORRECTION

PATENT NO. : 5,820,612
DATED : October 13, 1998
INVENTOR(S) : Todd A. Berg

It is certified that error appears in the above-identified patent and that said Letters Patent is hereby corrected as shown below:

Column 4, line 28, after "counterbore" insert --to provide a flexibility transition area to said joint--.

Column 5, line 5, after "counterbore" insert --to provide a flexibility transition area to said joint--.

Signed and Sealed this

Sixteenth Day of February, 1999

Attest:

*Attesting Officer*

*Acting Commissioner of Patents and Trademarks*